(12) United States Patent
Vartiainen

(10) Patent No.: US 7,795,492 B2
(45) Date of Patent: Sep. 14, 2010

(54) ABSORBENT ARTICLE HAVING OPENINGS IN THE ABSORBENT BODY

(75) Inventor: Kent Vartiainen, Lerum (SE)

(73) Assignee: SCA Hygiene Products AB, Gothenburg (SE)

( * ) Notice: Subject to any disclaimer, the term of this patent is extended or adjusted under 35 U.S.C. 154(b) by 692 days.

(21) Appl. No.: 10/227,442

(22) Filed: Aug. 26, 2002

(65) Prior Publication Data

US 2003/0045851 A1    Mar. 6, 2003

Related U.S. Application Data

(60) Provisional application No. 60/315,999, filed on Aug. 31, 2001.

(51) Int. Cl.
*A61F 13/15* (2006.01)
*A61F 13/20* (2006.01)

(52) U.S. Cl. .................................. 604/378; 604/385.01

(58) Field of Classification Search ......... 604/378–383, 604/385.01, 385.101
See application file for complete search history.

(56) References Cited

U.S. PATENT DOCUMENTS

| | | | |
|---|---|---|---|
| 3,620,894 A | 11/1971 | Oates | |
| 3,814,101 A | 6/1974 | Kozak | |
| 3,994,299 A | 11/1976 | Karami | |
| 4,276,338 A * | 6/1981 | Ludwa et al. | 428/137 |
| 4,592,751 A * | 6/1986 | Gegelys | 604/368 |
| 4,780,352 A * | 10/1988 | Palumbo | 428/138 |
| 5,533,991 A | 7/1996 | Kirby et al. | |
| 5,788,684 A * | 8/1998 | Abuto et al. | 604/368 |
| 5,846,231 A | 12/1998 | Fujioka et al. | |
| 5,961,505 A | 10/1999 | Coe et al. | |
| 6,241,714 B1 * | 6/2001 | Raidel et al. | 604/378 |
| 6,410,822 B1 * | 6/2002 | Mizutani | 604/380 |
| 6,432,094 B1 * | 8/2002 | Fujioka et al. | 604/385.01 |
| 6,458,111 B1 | 10/2002 | Onishi et al. | |
| 6,824,534 B2 * | 11/2004 | Mishima et al. | 604/385.01 |
| 2001/0037103 A1 * | 11/2001 | Onishi | 604/385.19 |

FOREIGN PATENT DOCUMENTS

| | | |
|---|---|---|
| AU | 2002330815 B2 | 10/2007 |
| JP | 05-253259 | 10/1993 |

(Continued)

OTHER PUBLICATIONS

Mexican Office Action dated Jan. 29, 2008 and partial English translation.

(Continued)

*Primary Examiner*—Michele Kidwell
(74) *Attorney, Agent, or Firm*—Buchanan Ingersoll & Rooney PC

(57) ABSTRACT

An absorbent article such as a nappy or an incontinence pad, with a liquid-permeable surface layer, a liquidtight surface layer, and a first absorbent body arranged between the surface layers and extending in longitudinal and transverse directions along the surface layers and also in a through-direction from the liquid-permeable surface layer towards the liquidtight surface layer. The first absorbent body has openings which extend in the through-direction. A second absorbent structure is arranged on that side of the first absorbent body facing away from the liquid-permeable surface layer. The liquid-permeable surface layer is attached to the second absorbent structure through the openings.

19 Claims, 3 Drawing Sheets

FOREIGN PATENT DOCUMENTS

| | | |
|---|---|---|
| JP | 08-191857 | 7/1996 |
| JP | 2000-051270 | 2/2000 |
| JP | 2000-333992 | 12/2000 |
| SE | 345378 | 5/1972 |
| SE | 432348 | 4/1984 |
| WO | 94/10956 | 5/1994 |
| WO | 96/20670 | 7/1996 |
| WO | WO 97/14388 | 4/1997 |
| WO | 99/25291 | 5/1999 |
| WO | 99/25550 * | 5/1999 |
| WO | WO 01/45616 A1 | 6/2001 |

OTHER PUBLICATIONS

English Translation of Notice of Reasons for Rejection in JP 2003-522424 dated Sep. 24, 2008.
Office Action issued on Jun. 5, 2009 in CA 2,459,174.
Polish Office Action dated Aug. 18, 2009 in Polish Patent Application No. P-367820.

* cited by examiner

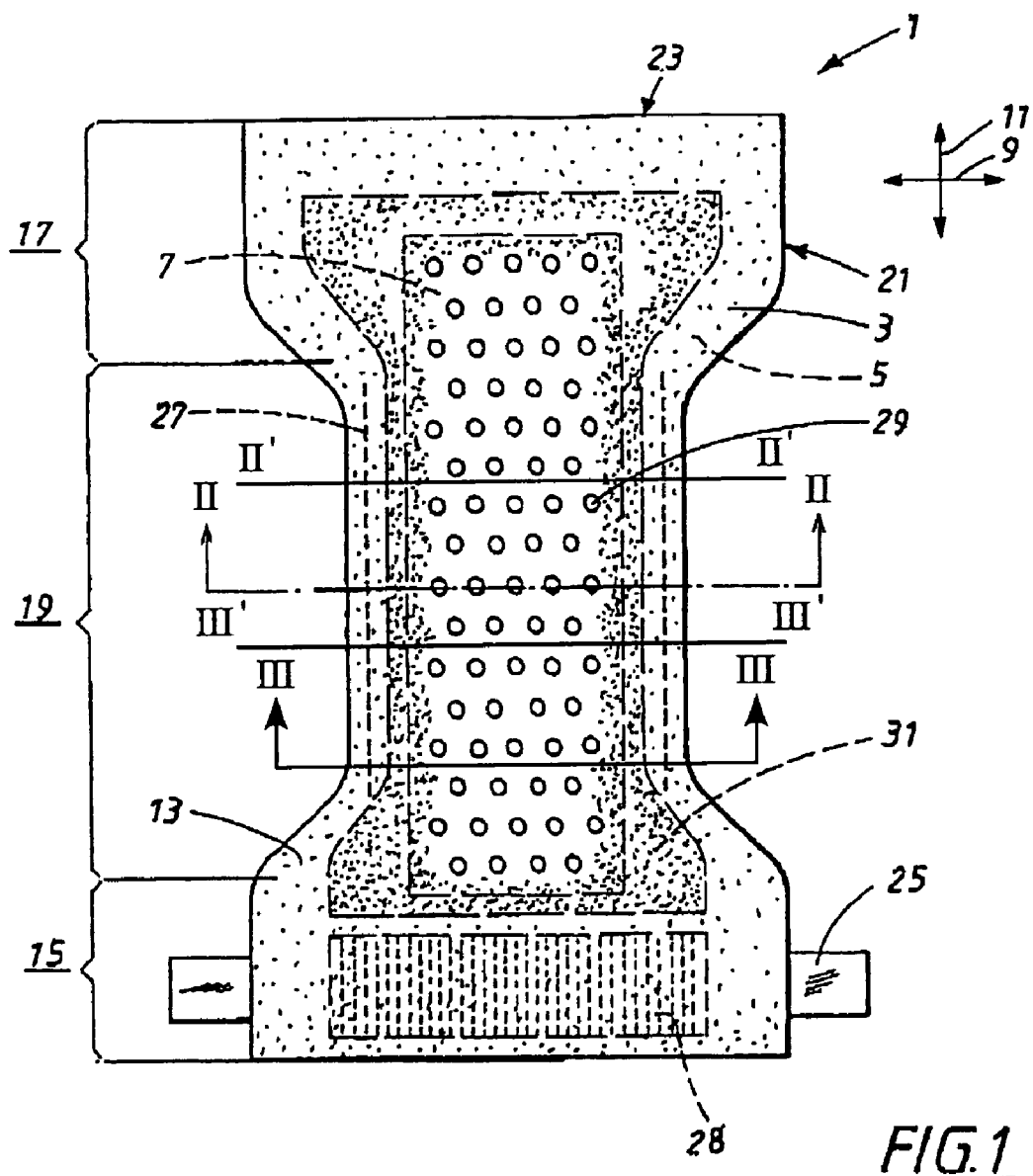
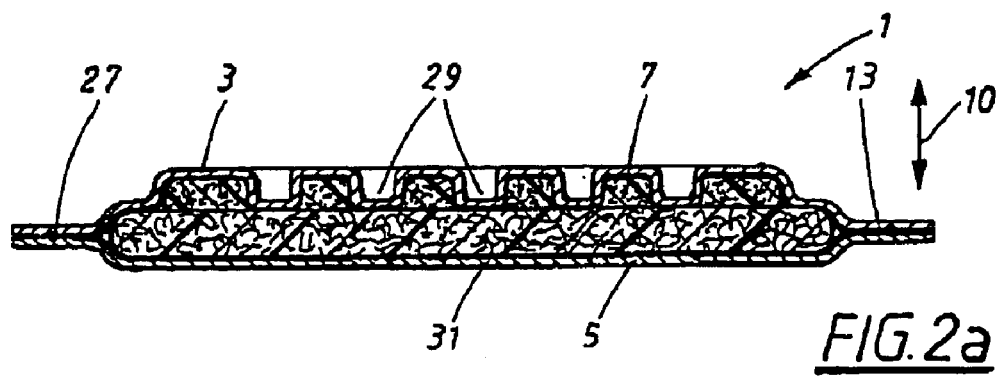
FIG. 1
FIG. 2a

ABSORBENT ARTICLE HAVING OPENINGS IN THE ABSORBENT BODY

This application claims priority under 35 U.S.C. §119 to U.S. Provisional Application No. 60/315,999 entitled ABSORBENT ARTICLE HAVING OPENINGS IN THE ABSORBENT BODY and filed on Aug. 31, 2001, the entire content of which is hereby incorporated by reference.

BACKGROUND

1. Field of the Invention

The present invention relates to an absorbent article, such as a nappy or an incontinence pad, comprising a liquid-permeable surface layer, a liquidtight surface layer and a first absorbent body arranged between the surface layers. The first absorbent body extends in a longitudinal direction and a transverse direction along the surface layers and also a through-direction from the liquid-permeable surface layer towards the liquidtight surface layer, the first absorbent body having openings which extend in the through-direction.

2. Related Art

U.S. Pat. No. 5,846,231 describes an absorbent article comprising a liquid-permeable surface layer attached to the liquidtight surface layer through openings in the form of cuts in the absorbent body. In order to obtain better spreading across the article, the cuts are arranged intermittently in a longitudinal direction also in addition to, as previously known, in a transverse direction. For effective spreading and handling of large quantities of urine and also more viscous liquids such as loose movements, however, this solution is inadequate.

WO 99/25291 describes an absorbent article comprising a receiving means intended to be positioned close to the anus and having a stated effective openness and also arranged over a storage layer for dealing with more viscous liquids such as loose movements. The liquid-permeable surface layer can be provided with holes. However, this solution is not adequate for effectively spreading and storing both urine and movements either.

WO 96/20670 describes an absorbent article comprising an absorbent body having receiving spaces which may be in the form of holes through the absorbent body. Areas in the absorbent body adjacent to the receiving spaces consist of a material which, when wetted, increases in thickness in a direction through the article at right angles to the receiving surface of the article. The spaces are arranged between an overlying layer and an underlying layer.

SUMMARY

One object is to provide an absorbent article with an improved capacity to deal with both urine and more viscous liquids such as loose bowel movements. Another object of the present invention is to produce a drier contact surface against the skin when urine and more viscous liquids are dealt with.

In accordance with embodiments of the invention, an absorbent article of the type referred to in the introduction has been produced. An absorbent article is characterized mainly in that a second absorbent structure is arranged on that side of the first absorbent body facing away from the liquid-permeable surface layer, and in that the liquid-permeable surface layer is attached to the second absorbent structure through the openings.

"Attached to" means that the materials are joined together with one another directly, or indirectly via an intermediate material. The attachment can be in the form of, for example, ultrasonic welding, thermal welding or glue.

The liquid-permeable surface layer can include any known material intended for the purpose of allowing liquid to pass through to an underlying layer. Examples of such materials are non-woven material, perforated plastic film, perforated hydrophobic materials, net or the like. The surface layer can also include a laminate of two or more layers of the same material or different materials.

According to an embodiment of the invention, the liquid-permeable surface layer is not attached to the first absorbent body. The liquid-permeable surface layer in modern known absorbent articles is usually attached to an underlying absorbent structure by means of glue. This is done inter alia so that the absorbent structure will not move or form lumps. By virtue of attaching the liquid-permeable surface layer to the second absorbent body, it is not necessary to glue the liquid-permeable surface layer to the first absorbent structure. Problems such as glue breakthrough, owing to the application of too much glue to the article during manufacture, and attendant skin irritations or restricted liquid permeability as pores in the liquid-permeable surface layer are obstructed by glue, can thus be eliminated. Other problems such as stoppages during manufacture of the article on account of glue in the machines, and impaired absorption capacity as a result of the glue having blocked pores in the absorbent body can also be reduced. Advantageously, it is possible to use thin liquid-permeable surface layers without the pores of the surface layer being clogged or glue penetrating the material, as a result of which better permeability can be obtained. The liquid-permeable surface layer can thus have a maximum weight per unit area of 20 g/m$^2$.

According to an embodiment of the invention, a liquid transport layer is arranged between the liquid-permeable surface layer and the first absorbent body. In this embodiment, the liquid transport layer is also attached to the second absorbent structure through the openings through the first absorbent body. The liquid-permeable surface layer is attached indirectly to the second absorbent structure through the liquid transport layer lying between the surface layer and the second absorbent structure.

According to an embodiment of the invention, the second absorbent structure comprises a liquid-penetrable layer arranged on the liquid-receiving side of the structure, to which layer the liquid-permeable surface layer is attached. The liquid-permeable layer can be formed of any known material intended for the purpose of allowing liquid to pass through to an adjacent layer. Examples of such materials are non-woven material, perforated plastic film, perforated hydrophobic materials, net or the like. The layer can also be a laminate of two or more layers of the same material or different materials. As this layer is not in direct contact with skin, it can also advantageously include a hydrophilic material or a hydrophilicized hydrophobic material and thus rapidly allow liquid to pass through to underlying layers. Examples of suitable hydrophilic materials are rayon or cotton. Examples of methods of hydrophilicizing hydrophobic materials are to treat the material with wetting agent, flame-treatment, corona or plasma. The second absorbent structure can be a liquid-penetrable layer.

The liquid-penetrable layer does not have to be attached to underlying layers such as, for example, any other parts of the absorbent structure, or to an underlying third absorbent structure or alternatively to the liquidtight surface layer in embodiments in which the second absorbent structure consists of only a liquid-penetrable layer. By virtue of the fact that the liquid-penetrable layer is not attached to the underlying layer, a flexible space is obtained between the liquid-penetrable layer and the underlying layer. The liquid-permeable surface layer and the liquid-penetrable layer can then preferably have holes which are arranged at the openings through the absorbent body. Movements and urine can thus collect in the flexible space between the liquid-penetrable layer and the underlying layer after passing through the holes and openings.

In the above paragraph, "underlying layer" means that the layer is arranged on a side of the liquid-penetrable layer which faces away from a wearer during use.

In this context, "not attached to" means that the materials have not intentionally been joined together with one another during manufacture. However, the first absorbent body can, in an area closest to the attachment of the liquid-permeable surface layer to the second absorbent structure, be joined to either the liquid-permeable surface layer or the second absorbent structure or both. The materials can be joined together with one another along transverse and/or longitudinal side edges.

The liquid-permeable surface layer can have hydrophobic areas between the openings. Urine and movements then run down rapidly into the openings for collection before further spreading into absorbent structures and bodies. The liquid-permeable surface layer can thus provide a drier feeling during use. The liquid-permeable surface layer can include a perforated hydrophobic material, or the surface layer can be treated chemically so as to obtain a zoned hydrophobic surface in a manner which is previously known.

BRIEF DESCRIPTION OF THE FIGURES

FIG. 1 shows a plane view of a nappy according to an embodiment of the invention, FIG. 2a shows a section through the nappy in FIG. 1 along the line II-II according to a first embodiment.

DETAILED DESCRIPTION OF PREFERRED EMBODIMENTS

Figure 2B:
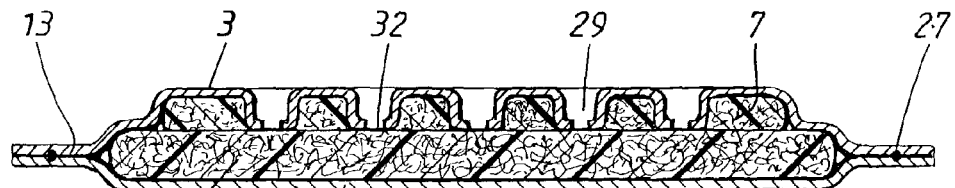
FIG. 2b shows a section through the nappy in FIG. 1 along the line II-II according to a second embodiment.

The nappy 1 shown in FIGS. 1 and 2 comprises a liquid-permeable surface layer 3, a liquidtight surface layer 5 and also a first absorbent body 7 arranged between the surface layers 3, 5. The nappy has a transverse direction 9 and a longitudinal direction 11 in a plane. The nappy also has a through-direction 10 at right angles to the longitudinal and the transverse direction.

The two surface layers extend outside the first absorbent body 7 in the transverse direction 9 and the longitudinal direction 11 and are interconnected in the projecting portions 13 by, for example, glue or thermal or, alternatively, ultrasonic welding.

The liquid-permeable surface layer 3 can be any known material intended for the purpose of allowing liquid to pass through to an underlying layer. Examples of such materials are non-woven material, perforated plastic film, perforated hydrophobic materials, net or the like. The surface layer can also be a laminate of two or more layers of the same material or different materials. The liquid-permeable surface layer can be a stretchable material, either elastically stretchable or inelastically stretchable.

The liquidtight surface layer 5 can be any material intended for the purpose of resisting liquid penetration. Examples of such materials are plastic films, laminates of a number of layers of non-woven material and/or plastic film and similar materials. It is an advantage if the material has the capacity to allow water vapour to pass through and thus exhibits breathability.

The nappy 1 has an elongate shape with a rear portion 15 intended to lie close to a wearer at the rear during use, a front portion 17 intended to lie close to the wearer at the front during use and a crotch portion 19 lying between the front portion 17 and the rear portion 15. The crotch portion 19 lying between the front portion 17 and the rear portion 15 is narrower than the rear portion 15 and the front portion 17, the nappy 1 having an hourglass shape. The nappy also has longitudinal side edges 21 and transverse end edges 23.

On the rear portion 15, the nappy has an attachment means 25 arranged along each longitudinal side edge 21 and intended to attach to a receiving area arranged on a side of the front portion 17 which faces outwards during use of the nappy. Such attachment means 25 are previously known and can comprise, for example, adhesive fastening means such as, for example, tape or mechanical fastening means such as, for example, touch and close fasteners. The receiving area can, for adhesive fastening means, be reinforced with a plastic film or, for mechanical fastening means, constitute a surface to which mechanical fastening means can attach, such as, for example, touch and close fasteners or non-woven material.

The invention is not limited by the above-described design or by the drawings. Within the scope of the invention, it is not necessary, for example, for the absorbent article to be provided with attachment means. An article having closed side portions such as, for example, nappy pants is also a possible embodiment of the invention. Absorbent inserts for application in liquidtight coverings are also possible embodiments of the invention. The design is of course not to be considered as being limited to the hourglass shape shown either.

The nappy 1 can also have a longitudinal elastic means 27 attached in a pretensioned state along each longitudinal side edge 21. The elastic means 27 are intended to seal against the legs of a wearer during use and thus provide better protection against leakage of liquids from the nappy. Along the end edge 23 on the rear portion 15, the nappy 1 can have a transverse elastic means 28 attached to the nappy in a pretensioned state. This transverse elastic means 28 constitutes the waist elastic. It is not necessary for the invention that the article has elastic means.

The first absorbent body can comprise one or more layers of the same absorbent material or different absorbent materials.

The first absorbent body is preferably designed so as to receive and transport liquid. It can then comprise a layer of a material which has large pores or capillaries so as to acquire a low resistance to liquid flow through the body. This layer suitably consists of a soft material which feels pleasant against the body of the wearer during use. Examples of materials which can be used are cellulose layers with a low degree of compression, in particular made of mechanical, thermomechanical or chemithermomechanical pulp (CTMP) or fibre mats and wadding made of other types of natural or synthetic fibres. It is also possible to use soft perforated or open-cell materials such as, for example, foam.

The first absorbent body can also include certain quantity of highly absorbent polymers, what are known as superabsorbents, in the form of fibres, particles, granules, film or the like. These superabsorbents are characterized by a great capacity to bind liquid in a quantity corresponding to several times their own weight.

The first absorbent body can also be material which expands greatly in the through-direction when wetted. The production of a suitable such material is described in WO 94/10956. The characteristic feature of this material is that it is produced by dry-forming flash-dried cellulose fibres to form a web with a weight per unit area of 30-2000 $g/m^2$ which is compressed to a density between 0.2 and 1 $g/m^3$, and that the web is incorporated as an absorbent structure into an absorbent article without subsequent defibration and fluff formation. Another example is cellulose fluff pulp, into which a certain quantity of superabsorbent material, preferably at least 10% by weight, has been mixed. Examples of other materials which can expand in the through-direction are compressed foamed materials and fibre wadding which partly return to their uncompressed size when wetted. The liquid-permeable surface layer preferably consists of a stretchable material as the first absorbent body comprises an expandable material.

The first absorbent body 7 can have a number of openings 29 in the form of rounded holes. These openings extend through the first absorbent body 7 in the through-direction 10 from that side of the absorbent body which faces the wearer during use of the article to that side of the absorbent body which faces away from the wearer during use of the article. The shape of the openings is not critical, but the openings should be sufficiently large for collecting movements. The openings 29 can also be in the form of cuts through the absorbent body.

The openings 29 can be arranged over essentially the whole of the first absorbent body 7, as in FIG. 1. However, this is not necessary for the invention. The openings can instead be arranged, for example, within one or more areas of the absorbent body, for example within the front portion, the rear portion, the crotch portion or parts of these. Nor do the openings have to be the same size. For example, the openings in the front portion and the rear portion can be larger than the openings in the crotch portion, or vice versa. The openings in the rear portion can be larger than the openings in the front portion, or vice versa. The openings within an area can also be of different size. The number of openings is preferably at least three, preferably more, but only one or two opening(s) are also to be seen as possible embodiments of the invention.

In accordance with an embodiment of the invention, the nappy 1 can comprise a second absorbent structure 31 arranged between the first absorbent body 7 and the liquidtight surface layer 5.

The liquid-permeable surface layer 3 is attached to the second absorbent structure 31 by means of, for example, ultrasound in areas which are constituted by the through-openings 29 in the first absorbent body 7. Thermal welding or gluing are examples of other possible ways of attaching the liquid-permeable surface layer to the second absorbent body 31.

It is not necessary for the first absorbent body to be attached to the second absorbent structure in any other way than by virtue of the liquid-permeable surface layer being attached to the second absorbent structure in the openings through the first absorbent body, as a result of which the first absorbent body is held in place between the liquid-permeable surface layer and the second absorbent structure. The openings then constitute a flexible space for collecting movements as they have the possibility to expand in the transverse, longitudinal and/or through-direction of the nappy because the first absorbent body is not attached to adjacent layers between the openings, as a result of which its structure acquires a certain flexibility/mobility.

The second absorbent structure can comprise a liquid-penetrable layer and/or one or more layers of the same absorbent material or different absorbent materials.

The second absorbent structure can advantageously function as a spreading layer and storage layer and suitably comprises a material of great density and with a great liquid-spreading and liquid-retaining capacity. An example of a suitable material is chemically produced cellulose fluff pulp (CP) with a weight per unit area of roughly 400 $g/m^2$. The dry-formed fibrous layer mentioned above and described in WO 94/10956 can also advantageously be used. The liquid-spreading layer can be provided with compression patterns so as to guide the liquid transport along the compressions.

The second absorbent structure 31 can comprise a material with an open structure which has large pores or capillaries so as to acquire a low resistance to liquid flow through the body. Examples of materials which can be used are cellulose layers with a low degree of compression or fibre mats and wadding made of other types of natural or synthetic fibres. It is also possible to use soft perforated or open-cell materials. Folded materials, undulating materials or materials shaped into an open structure in another way can also be used.

The second absorbent structure can also advantageously comprise some form of superabsorbent. A suitable content of superabsorbent can be at least 10% by weight, preferably 10-60% by weight.

The second absorbent structure can comprise a liquid-penetrable layer. This can consist of any known material suitable for the purpose. Examples of such materials are non-woven materials, perforated plastic films, net etc. The layer can be made of a hydrophilic material such as, for example, corona-treated non-woven or rayon.

The embodiment shown in FIG. 2a of a cross section of the nappy in FIG. 1 along the line II-II comprises a first absorbent body 7 comprising a layer which has large pores or capillaries so as to acquire a low resistance to liquid flow through the body. This layer suitably consists of a soft material which feels pleasant against the body of the wearer during use. Examples of materials which can be used are cellulose layers with a low degree of compression, in particular made of mechanical, thermomechanical or chemithermomechanical pulp (CTMP) or fibre mats and wadding made of other types of natural or synthetic fibres. It is also possible to use soft perforated or open-cell foamed materials. A liquid-permeable surface layer 3, which during use is arranged on that side of the first absorbent body 7 which faces a wearer of the nappy during use, is attached to a second absorbent structure 31 positioned on that side of the first absorbent body 7 which faces away from the wearer during use through openings 29 through the first absorbent body. These openings 29 extend through the first absorbent body 7 in a through-direction 10 from that side of the first absorbent body 7 which faces the wearer during use of the article to that side of the absorbent body which faces away from the wearer during use of the article.

The second absorbent structure 31 comprises, for example, a spreading layer/storage layer made of a material of great density and with a great liquid-spreading and liquid-retaining capacity. An example of a suitable material is chemically produced cellulose fluff pulp (CP) with a weight per unit area of roughly 400 g/m$^2$. The dry-formed fibrous layer mentioned above and described in WO 94/10956 can also advantageously be used. The second absorbent structure preferably also comprises 10-60% by weight superabsorbents.

The liquid-permeable surface layer in the embodiment shown in FIG. 2b of a cross section of the nappy in FIG. 1 along the line II-II has holes 32 at the openings 29 through the first absorbent body 7. The holes in FIG. 2b are arranged straight over the openings through the first absorbent body. These holes can be formed in conjunction with the joining together of the liquid-permeable surface layer and the second absorbent structure, for example during welding, or a previously perforated liquid-permeable surface layer can be used. It is not necessary for the holes through the liquid-permeable surface layer to be arranged straight above the openings through the first absorbent body, but the holes should be positioned at the openings in such a manner as makes it possible for urine and/or movements to pass through the holes after collecting in the openings. The holes can be positioned, for example, so that they are directed towards the first absorbent body.

The holes 32 and the openings 29 are preferably sufficiently large for movements to be capable of passing through.

The second absorbent structure 31 in FIG. 2b suitably comprises, on that side of the structure which faces the first absorbent body, a layer of a material which has large pores or capillaries so as to acquire a low resistance to liquid flow through the body. The layer preferably has an open structure suitable for collecting movements. Examples of materials which can be used are cellulose layers with a low degree of compression or fibre mats and wadding made of other types of natural or synthetic fibres. It is also possible to use soft perforated or open-cell materials. Folded materials, undulating materials or materials shaped into an open structure in another way can also be used.

Figure 2C:
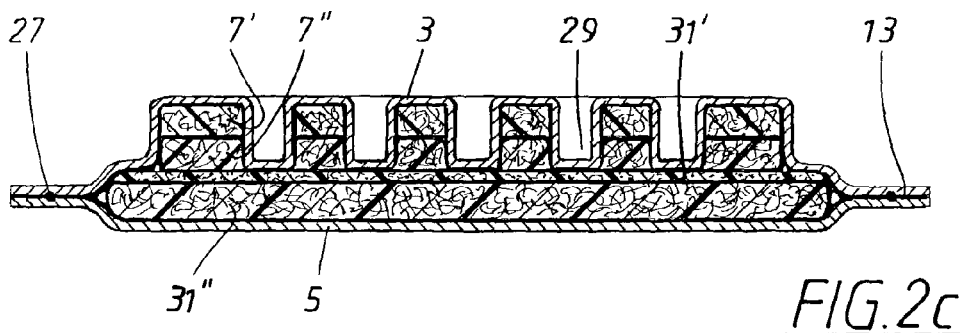
FIG. 2c shows a section through the nappy in FIG. 1 along the line II-II according to a third embodiment.

The first absorbent body 7 in the embodiment shown in FIG. 2c of a cross section of the nappy in FIG. 1 along the line II-II comprises a first layer 7' of a material which has large pores or capillaries so as to acquire a low resistance to liquid flow through the body. This first layer 7' suitably consists of a soft material which feels pleasant against the body of the wearer during use. This first layer 7' is positioned against the liquid-permeable surface layer 3. The first absorbent body 7 also comprises a second absorbent layer 7" which is more open or porous than the first layer 7' and consists of a material which has large pores or capillaries so as to acquire a low resistance to liquid flow through the layer. Examples of materials which can be used are cellulose layers with a low degree of compression or fibre mats and wadding made of other types of natural or synthetic fibres. It is also possible to use soft perforated or open-cell materials. Folded materials, undulating materials or materials shaped into an open structure in another way can also be used.

A liquid-permeable surface layer 3, which during use is positioned on that side of the first absorbent body 7 which faces a wearer of the nappy during use, is attached to a second absorbent structure 31 positioned on that side of the first absorbent body 7 which faces away from the wearer during use through openings 29 through the first absorbent body. These openings 29 extend through the first absorbent body 7 in a through-direction 10 from that side of the first absorbent body 7 which faces the wearer during use of the article to that side of the absorbent body which faces away from the wearer during use of the article.

The second absorbent structure 31 in FIG. 2c can include, for example, a first layer 31' of hydrophilic non-woven material with a good admission capacity facing the first absorbent body 7 and a second layer 31" of a material of great density and with a great liquid-spreading and liquid-retaining capacity facing away from the first absorbent body. An example of a suitable material is chemically produced cellulose fluff pulp (CP) with a weight per unit area of roughly 400 g/m$^2$. The dry-formed fibrous layer mentioned above and described in WO 94/10956 can also advantageously be used. The absorbent structure can preferably comprise 10-60% by weight superabsorbents.

Figure 2D:
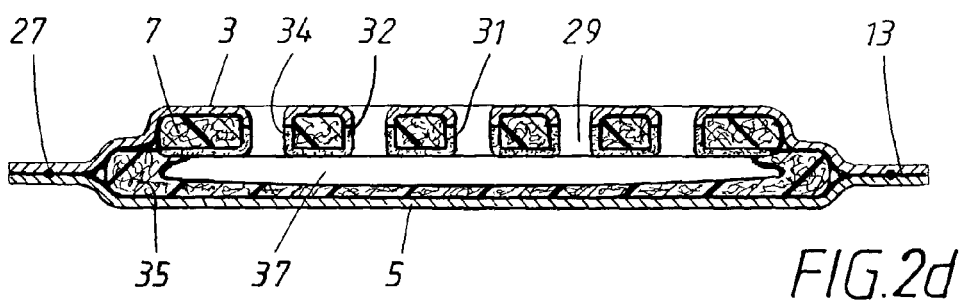
FIG. 2d shows a section through the nappy in FIG. 1 along the line II-II according to a fourth embodiment.
Figure 3:
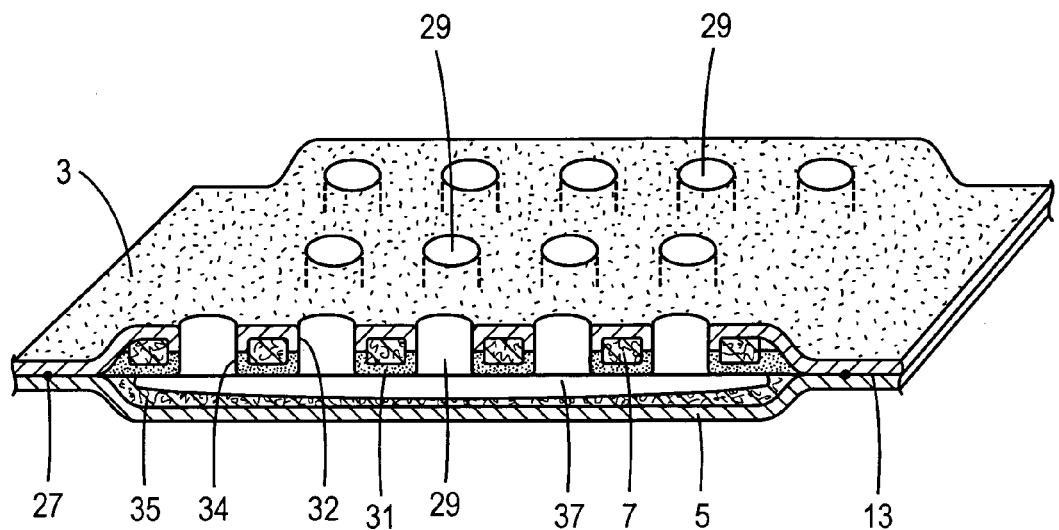
FIG. 3 shows a section through the nappy in FIG. 1 along the line II-II through II'-II' according to the fourth embodiment, which illustrates the perspective view of FIG. 2d (in combination with FIG. 1)
Figure 4:
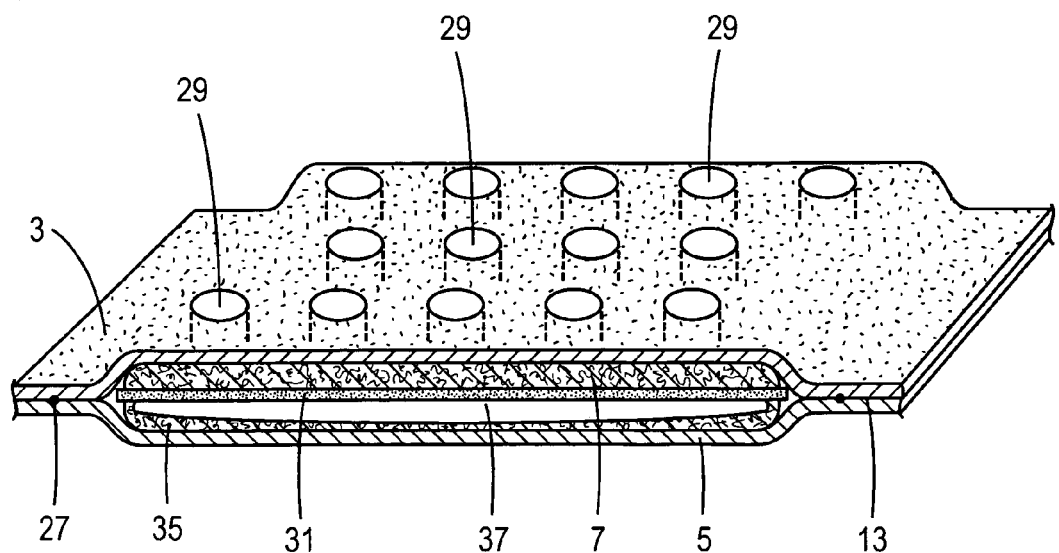
FIG. 4 shows a section through the nappy in FIG. 1 along the lines III-III through III'-III' according to the fourth embodiment, which shows a different section from FIG. 2d (in combination with FIG. 1) of the same fourth embodiment.

In FIGS. 2d, 3 and 4, a liquid-permeable surface layer 3 is attached to a second absorbent structure 31 in the form of a liquid-penetrable layer positioned on that side of the first absorbent body 7 which faces away from the wearer during use through openings 29 through the absorbent body. These openings 29 extend through the first absorbent body 7 in a through-direction 10 from that side of the first absorbent body 7 which faces the wearer during use of the article to that side of the absorbent body which faces away from the wearer during use of the article. At holes 32 through the liquid-permeable surface layer 3, the surface layer 3 is attached to the liquid-penetrable layer 31 at holes 34 through the layer 31, which holes 32, 34 are positioned at the openings 29 through the first absorbent body 7 so that urine and/or motions can pass through the openings 29 and the holes 32, 34.

As illustrated in FIG. 3, which illustrates a perspective view in combination with FIG. 1, openings 29 are spaced throughout the nappy 1, wherein the liquid-permeable surface layer 3 is attached to the second absorbent structure 31 at locations within the openings 29 that extend through the first absorbent body 7. As illustrated in FIG. 4, the liquid-permeable surface layer 3 is on top of the first absorbent body 7, which in turn is on top of the second absorbent structure 31.

As illustrated in FIG. 4, the liquid-permeable surface layer 3 sits on top of the first absorbent body 7, which in turn sits on top of the second absorbent structure 31. The openings 29 which are formed through the liquid-permeable surface layer 3, the first absorbent body 7, and the second absorbent structure 31, penetrates all the way from the top surface of the nappy 1 (i.e., the liquid-permeable surface layer 3) through to space 37 formed between the second absorbent structure 31 and a third absorbent structure 35.

Further, in FIGS. 1, 3 and 4, a single apertured sheet 3 is illustrated with a plurality of through-hole openings 29 extending therethrough. As also illustrated in FIGS. 1, 2d, 3 and 4, a first absorbent body 7 having a plurality of through-hole openings 29, which extend in the through-direction, is illustrated along with a second absorbent structure 31, which comprises a liquid-penetrable layer, is attached to the liquid-permeable surface layer 3 through the openings 29, wherein the through-hole openings 29 extend through the first absorbent body 7 into the second absorbent structure 31 and into a space 37 beneath the second absorbent structure 31.

A third absorbent structure 35 is positioned on that side of the second absorbent structure which faces away from the wearer during use. The third absorbent structure 35 in FIG. 2d comprises, for example, a layer of a material which has large pores or capillaries so as to acquire a low resistance to liquid flow through the body. The layer preferably has an open structure suitable for collecting movements. Examples of materials which can be used are cellulose layers with a low degree of compression or fibre mats or wadding made of other types of natural or synthetic fibres. It is also possible to use soft perforated or open-cell materials. Folded materials, undulating materials or materials shaped into an open structure in another way can also be used.

The third absorbent structure 35 can comprise a material of great density and with a great liquid-spreading and liquid-retaining capacity. An example of a suitable material is chemically produced cellulose fluff pulp (CP) with a weight per unit area of roughly 400 g/m². The dry-formed fibrous layer mentioned above and described in WO 94/10956 can also advantageously be used. The third absorbent structure can also comprise superabsorbents, preferably in a quantity of 10-60% by weight.

The second absorbent structure 31 in FIG. 2d is not attached to the third absorbent structure 35, a space 37 being formed between the second absorbent structure and the third absorbent structure for collecting motions after the motions have passed through the openings through the layers and the first absorbent body. Openings 29 allow motions to pass from above the liquid-permeable surface layer 3 through openings 29 into a space 37.

Figure 2E:
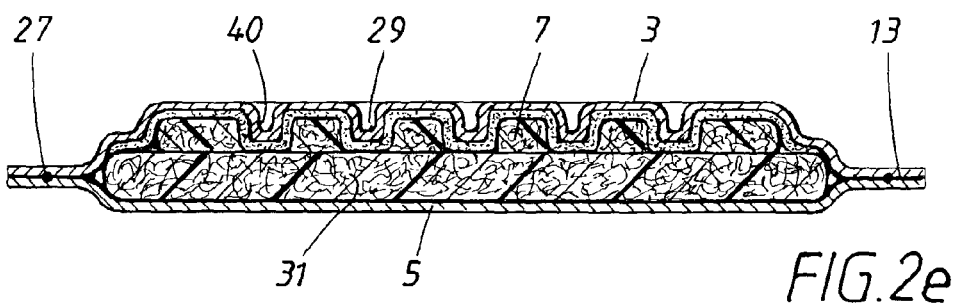
FIG. 2e shows a section through the nappy in FIG. 1 along the line II-II according to a fifth embodiment.

The embodiment shown in FIG. 2e of a cross section of the nappy in FIG. 1 along the line II-II comprises a liquid transport layer 40 arranged between the liquid-permeable surface layer 3 and the first absorbent body 7. In FIG. 2e, both the liquid-permeable surface layer 3 and the liquid transport layer 40 are attached to the second absorbent structure 31 through openings 29 which extend in a through-direction through the first absorbent body 7. The liquid-permeable surface layer 3 is indirectly attached to the second absorbent structure by the liquid transport layer 40 lying between the liquid-permeable surface layer 3 and the second absorbent structure 31.

The liquid transport layer 40 preferably is a material which has large pores or capillaries so as to acquire a low resistance to liquid flow through the body. The liquid transport layer suitably can be a soft material which feels pleasant against the body of the wearer during use. Examples of materials which can be used are cellulose layers with a low degree of compression or fibre mats and wadding made of other types of natural or synthetic fibres. It is also possible to use soft perforated or open-cell materials, for example foam.

Figure 2F:
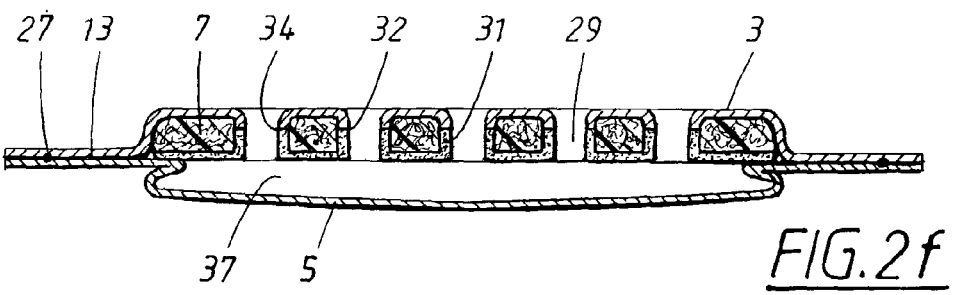
FIG. 2f shows a section through the nappy in FIG. 1 along the line II-II according to a sixth embodiment.

In FIG. 2f, a liquid-permeable surface layer 3 is attached to a second absorbent structure 31 in the form of a liquid-penetrable layer positioned on that side of the first absorbent body 7 which faces away from the wearer during use through openings 29 through the absorbent body. These openings 29 extend through the first absorbent body 7 in a through-direction 10 from that side of the first absorbent body 7 which faces the wearer during use of the article to that side of the absorbent body which faces away from the wearer during use of the article. At holes 32 through the liquid-permeable surface layer, the surface layer is attached to the liquid-penetrable layer at holes 34 through the layer, which holes 32, 34 are positioned at the openings 29 through the first absorbent body so that urine and/or movements can pass through the openings 29 and the holes 32, 34.

A liquidtight surface layer 5 is arranged on that side of the liquid-penetrable layer which faces away from the wearer during use. The second absorbent structure 31 in FIG. 2f is not attached to the liquidtight surface layer 5, a space 37 being formed between the second absorbent structure and the liquidtight surface layer 5 for collecting movements and urine after passing through the openings through the layers and the first absorbent body. Liquid can then also be absorbed into the first absorbent body from that side thereof which faces the liquidtight surface layer through the liquid-penetrable layer.

The invention is not to be considered as being limited to the embodiments indicated above, but a large number of modifications are possible within the scope of the following patent claims.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An absorbent article comprising:
   a liquid-permeable surface layer;
   a liquidtight surface layer;
   a first absorbent body that is arranged between the surface layers and extending in a longitudinal direction and a transverse direction along the surface layers and also a through-direction from the liquid-permeable surface layer towards the liquidtight surface layer, the first absorbent body comprising a single apertured layer with a plurality of through-hole openings extending therethrough; and
   a second absorbent structure arranged on a side of the first absorbent body which faces away from the liquid-permeable surface layer, wherein the liquid-permeable surface layer is attached to the second absorbent structure within the openings.

2. The absorbent article according to claim 1, wherein the liquid-permeable surface layer is not attached to the first absorbent body.

3. The absorbent article according to claim 1, the first absorbent body is not attached to the second absorbent structure.

4. The absorbent article according to claim 1, wherein the openings are rounded holes.

5. The absorbent article according to claim 1, wherein the liquid-permeable surface layer has holes arranged at the openings through the first absorbent body so that urine or movements can pass through the holes and the openings.

6. The absorbent article according to claim 1, wherein the liquid-permeable surface layer comprises hydrophobic areas between the openings through the first absorbent body.

7. The absorbent article according to claim 1, wherein the liquid-permeable surface layer has a maximum weight per unit area of 20 g/m².

8. The absorbent article according to claim 1, wherein a liquid transport layer is arranged between the liquid-permeable surface layer and the first absorbent body, the liquid transport layer also being attached to the second absorbent structure through the openings.

9. The absorbent article according to claim 1, wherein the absorbent article is a nappy or an incontinence pad.

10. An absorbent article comprising:
    a liquid-permeable surface layer;
    a liquidtight surface layer;
    a first absorbent body that is arranged between the surface layers and extending in a longitudinal direction and a transverse direction along the surface layers and also a through-direction from the liquid-permeable surface layer towards the liquidtight surface layer, the first absorbent body having a plurality of through-hole openings which extend in the through-direction; and
    a second absorbent structure comprising a liquid-penetrable layer arranged on a side of the first absorbent body which faces away from the liquid-permeable surface layer, wherein the liquid-permeable surface layer is attached to the liquid-penetrable layer within the openings, wherein the through-hole openings extend through the first absorbent body.

11. The absorbent article according to claim 10, wherein the liquid-permeable surface layer is not attached to the first absorbent body.

12. The absorbent article according to claim 10, the first absorbent body is not attached to the liquid-penetrable layer.

13. The absorbent article according to claim 10, wherein the liquid-permeable surface layer has a maximum weight per unit area of 20 g/m$^2$.

14. The absorbent article according to claim 10, wherein a liquid transport layer is arranged between the liquid-permeable surface layer and the first absorbent body, the liquid transport layer also being attached to the liquid-penetrable layer through the openings.

15. The absorbent article according to claim 10, further comprising a flexible space formed between the liquid-penetrable layer and the liquidtight surface layer.

16. The absorbent article according to claim 1, wherein the openings comprise cylindrical holes which extend in the through-direction.

17. The absorbent article according to claim 10, further comprising a third absorbent structure that is arranged between the second absorbent structure and the liquidtight surface layer.

18. The absorbent article according to claim 10, wherein the openings comprise cylindrical holes which extend in the through-direction.

19. An absorbent article comprising:
a liquid-permeable surface layer;
a liquidtight surface layer;
a first absorbent body that is arranged between the surface layers and extending in a longitudinal direction and a transverse direction along the surface layers and also a through-direction from the liquid-permeable surface layer towards the liquidtight surface layer, wherein the first absorbent body includes through-hole openings which extend through the first absorbent body; and
a second absorbent structure arranged on a side of the first absorbent body which faces away from the liquid-permeable surface layer, wherein the liquid-permeable surface layer is attached to the second absorbent structure within the openings.

* * * * *